United States Patent [19]

Ohlson et al.

[11] Patent Number: 4,679,223
[45] Date of Patent: Jul. 7, 1987

[54] METHOD FOR DAMPING THE NATURAL OSCILLATIONS OF A PILLAR-STAND CARRYING X-RAY EQUIPMENT, OCCURING WHEN MAKING POSITIONAL ADJUSTMENTS THERETO; AND A PILLAR STAND

[75] Inventors: Carl-Eric Ohlson, Solna; Günther Behnke, Skärholmen, both of Sweden

[73] Assignee: AO Medical Products AB, Stockholm, Sweden

[21] Appl. No.: 726,895
[22] PCT Filed: Aug. 16, 1984
[86] PCT No.: PCT/SE84/00278
§ 371 Date: Apr. 23, 1985
§ 102(e) Date: Apr. 23, 1985
[87] PCT Pub. No.: WO85/01181
PCT Pub. Date: Mar. 14, 1985

[30] Foreign Application Priority Data

Aug. 25, 1983 [SE] Sweden ............................ 8304617

[51] Int. Cl.⁴ ............................................. H05G 1/02
[52] U.S. Cl. ..................................... 378/195; 378/197
[58] Field of Search ............... 378/193, 195, 196, 197; 248/559, 636

[56] References Cited

U.S. PATENT DOCUMENTS

| | | | |
|---|---|---|---|
| 2,778,948 | 1/1957 | Berger | 378/196 |
| 3,803,418 | 4/1974 | Holstrom | 378/196 |
| 4,050,551 | 9/1977 | Schmedemann et al. | 378/91 |
| 4,181,347 | 1/1980 | Clark | 378/199 |
| 4,287,424 | 9/1981 | Tomita et al. | 378/11 |
| 4,365,343 | 12/1982 | Grady et al. | 378/197 |
| 4,420,134 | 12/1983 | Flannelly | 248/559 |

Primary Examiner—Janice A. Howell
Attorney, Agent, or Firm—Fleit, Jacobson, Cohn & Price

[57] ABSTRACT

A movably mounted pillar-stand for carrying X-ray equipment, the pillar-stand preferably celling-suspended and having a pendulum arrangement or the like for the purpose of damping natural oscillatory movements. When natural oscillatory movements occur in the pillar-stand when making positional adjustment thereto, the natural oscillatory movement of the stand is effectively extinguished within the space of some few seconds by a damped, counter-directional pendulating movement imparted to the pendulating arrangement by means of the natural oscillatory motion of the stand.

5 Claims, 6 Drawing Figures

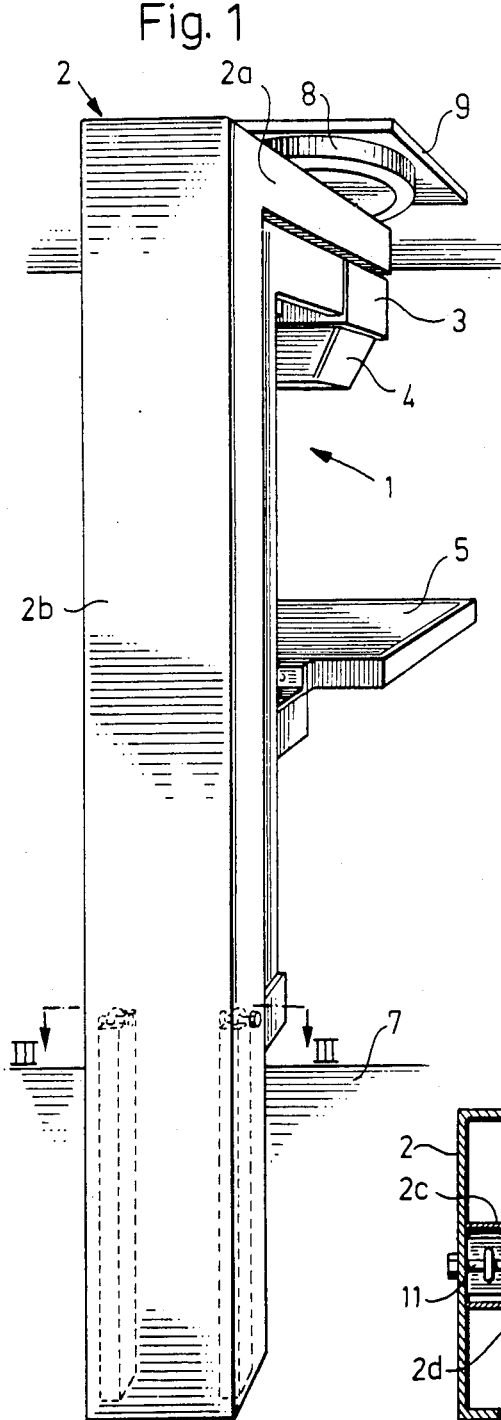
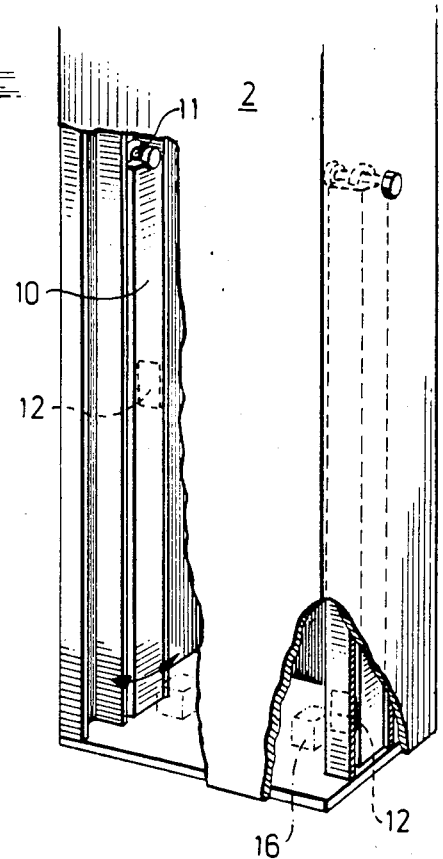
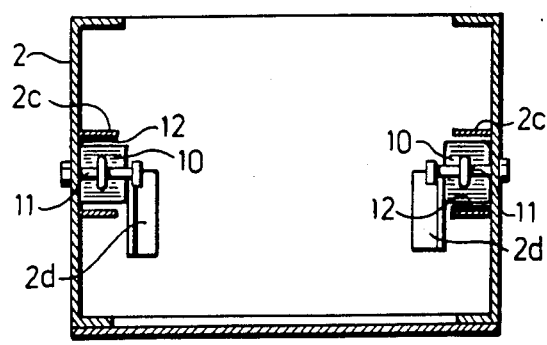

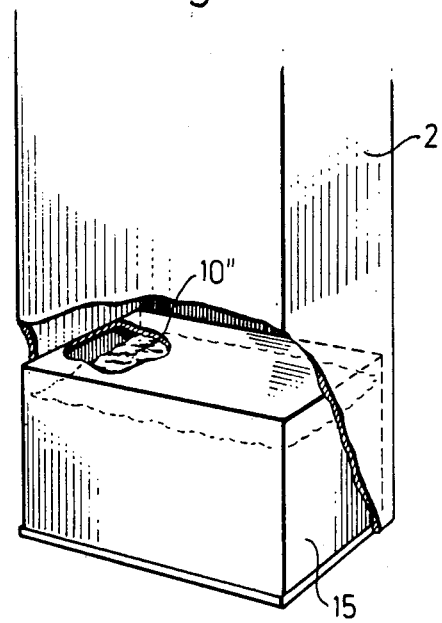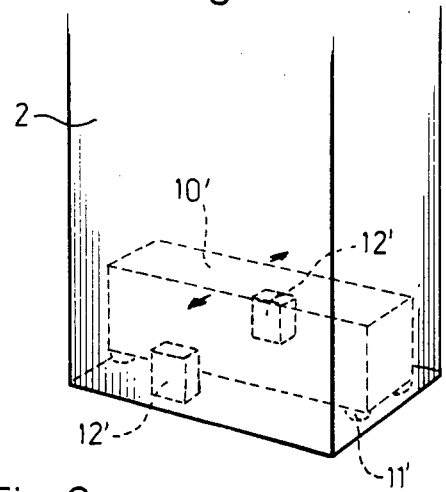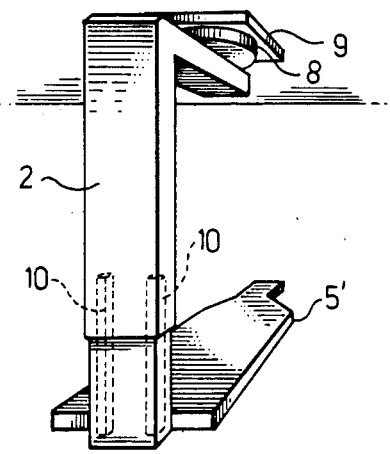

METHOD FOR DAMPING THE NATURAL OSCILLATIONS OF A PILLAR-STAND CARRYING X-RAY EQUIPMENT, OCCURING WHEN MAKING POSITIONAL ADJUSTMENTS THERETO; AND A PILLAR STAND

Field of invention

The present invention relates to a method for damping the natural vibrations and/or oscillations of movable pillar-stands carrying X-ray equipment, when making positional adjustments thereto.

Such a pillar-stand may be mounted to the ceiling, on the floor or on the wall of a room, and the equipment carried by said stand may comprise X-ray film exposure apparatus, a hospital bed or the like.

When the pillar-stand is suspended from the ceiling of a room, the stand often has an L-shape configuration, and the X-ray apparatus, hospital bed or the like is often positioned on a member which is movable in relation to the pillar-stand itself and which, either separately or together with the pillar-stand, has a U-shape, a C-shape or a similar shape.

A typical ceiling-hung pillar-stand often has the shape of an inverted L, and is mounted so as to be pivotable or adjustable about a vertical axis located in the upper part of said stand, at the end of the shorter leg thereof. The vertically extending, longer leg of the stand is provided with a further member which carries the X-ray equipment, such as exposure equipment and film-cassette holder or a hospital bed or the like.

This further member is normally arranged for vertical movement along the pillar-stand and is also mounted thereon for pivotal or rotary movement about a horizontal axis.

In the case of a typically ceiling-mounted pillar-stand of the aforedescribed kind, the height between ceiling and floor is 2.75 m, and the total height of the pillar-stand is slightly less than this measurement and measures, for example, about 2.5 m. When the pillar-stand carries X-ray equipment, the total weight may reach from 300 to 350 kg.

PRESENTATION OF THE UNDERLYING PROBLEMS RELEVANT TO THE INVENTION

One problem encountered with such pillar-stands, particularly with a pillar-stand mounted on the ceiling of a room, is that the stand can readily be set into free oscillation, e.g. when making positional adjustments, when the pillar-stand is swung about the vertical axis and/or the further part is swung about its horizontal axis.

Upon examination it has been found that the amplitude of this natural oscillatory movement in the case of a typical pillar-stand of the aforedescribed kind is about 2 mm, and that this amplitude is still close to 2 mm after a lapse of 12 seconds. After 36 seconds, the amplitude was found to have decreased to about 1 mm, and it took almost one minute before it could be said that the free oscillatory movement of the stand had ceased.

Tests have shown that when the pillar-stand is caused to oscillate or vibrate in an arbitrary direction — e.g. by kicking the base of a ceiling-suspended pillar-stand — the stand will relatively quickly begin to oscillate freely in one and the same plane, namely the plane exhibiting the lowest inertia against natural oscillation, in accordance with for example a central plane or symmetry plane which passes through the L-shaped stand and extends through its suspension point.

It will be understood that the course followed by natural oscillations of the aforedescribed kind constitutes a serious disadvantage, primarily because the X-ray exposure may be blurred as a result thereof. Thus, the phenomena of natural vibrations results, in turn, to the serious risk of necessitating the patient to be subjected to a repeated course of X-rays, with an increased X-ray dosage as a result thereof.

In order to further illustrate the decisive negative influence of the phenomena of natural oscillations on the final result, it can be mentioned that there are essentially three factors which contribute to the total blurring of an X-ray picture. These three factors are: geometric blurring blurring of the film system (limited resolution of the picture etc.), and movement blurring.

If these factors are assumed to have the numerical values a, b and c respectively, the total non-focussing or blurring effect is given by the expression $$\sqrt{a^2 + b^2 + c^2}$$

It will be seen herefrom that when one of these factors is substantially higher than the others, the higher factor will have a decisive effect on the end result.

By way of illustration it can be mentioned that a typical geometric non-sharpness may be as much as 0.2 mm in the case of an X-ray stand. A movement non-sharpness of a corresponding order of magnitude will typically occur at an exposure time of 0.01 seconds. Consequently, with an exposure time 10 times as long, i.e. 0.1 seconds, the movement non-sharpness will be 2 mm, i.e. will correspond to the amplitude of the natural oscillatory movement of a typical pillar-stand of the aforementioned kind. It is quite common to use much longer exposure times, up to 4–5 seconds.

When these values are inserted into the above formula, in which the film-blur is assumed to correspond to the value of the geometric blurring or non-sharpness, i e. 0.2, there is obtained a total blurring of $$\sqrt{0.2^2 + 0.2^2 + 2^2} = \sqrt{4.08} = 2.02 \text{ mm}$$

The conclusion was reached that even though expensive equipment having low geometric blurring, and a film having high resolution were used on a pillar-stand which exhibits high natural-oscillation amplitudes, the last mentioned factor will dominate, and hence the quality of the picture would be unsatisfactory.

The pertinent parts of the aforementioned are also true when a pillar-stand mounted, for example, on the ceiling of a room, carries a hospital bed, while the X-ray equipment is so supported as to substantially be free of natural oscillation.

Consequently, the problem upon which the present invention is based is also relevant in this case.

BACKGROUND ART

The aforementioned problem has earlier been observed, and various solutions have been proposed in an attempt to overcome the problem.

For example, there is described in SE-B-147.339 (Siemens-Reiniger-Werke) a method of eliminating oscillation of an X-ray apparatus by electro mechanical means. In the arrangement therein described there is used a support means which comprises at least two rigid members which can be adjusted relative to one another and which support against a part which is separate from the apparatus and which is stationary relative to the apparatus part to be supported. The stationary part may, for example, comprise the ceiling of a treatment room.

Such arrangements, which utilize a fixed support point externally of the X-ray stand, are normally particularly complicated and constitute a serious limitation to the extent to which the X-ray frame can be moved.

Consequently, such arrangements are unsuitable and have not met with wide use in modern X-ray stands.

Other types of arrangements are described in U.S. Pat. No. 4,287,424 (Tomita et al) which teaches a plurality of damping mechanisms in connection with tomography; U.S. Pat. No. 4,181,347 (Clark) which teaches vibration damping for mobile X-ray units; and U.S. Pat. No. 4,050,551 (Schmedemann et al) which teaches an arrangement for damping oscillations or vibrations in conjunction with counterweights.

None of these known arrangements provides a satisfactory solution to the problem of quickly damping effectively the natural oscillations of a pillar-stand carrying X-ray equipment.

BRIEF DISCLOSURE OF THE INVENTION

The present invention eliminates the aforementioned disadvantages and fulfils the aforesaid object, and its widest aspect is mainly characterized by applying a pivotable mass in said stand at a distance from the attachment point of said stand; and by causing said mass to execute a dampened oscillatory movement in a counter direction to said natural oscillations of the stand, such as to rapidly extinguish said natural oscillatory movement.

The aforementioned mass may comprise a pivotable body, for example a pendulum or a suitably journalled body of some other design, which can be caused to execute dampened oscillatory movements when the pillar-stand begins to oscillate at its natural frequency.

Alternatively, the mass may also comprise a quantity of liquid contained in a container suitably placed in the stand.

Such a liquid mass can be caused to execute counter-oscillations in any direction. An oscillation-damping pendulum, or some other kind of body, can also be arranged so that its counter-directed oscillatory movements can be effected in any desired direction.

Preferably, however, and particularly when the mass has the form of a body such as a pendulum or a suitably journalled weight, the body is arranged to swing in a plane in which the pillar-stand exhibits the lowest inertia against natural oscillations.

As beforementioned, as a rule the phenomenon whereby the natural oscillatory movement of the pillar-stand will take place in the direction exhibiting the lowest inertia against the oscillations will manifest itself irrespective of the direction in which the natural oscillatory movement of the stand begins. Consequently, the counter-directional oscillatory movement should take place in this direction.

In principle, the counter-directional oscillatory movement of the mass can be initiated and/or created in any desirable manner. Thus, if so desired, drive means may be provided for imparting the counter-directional movement to the mass. Preferably, however, the natural oscillatory movement of the stand itself is utilized to impart the counter-directional oscillatory movement to the mass. This provides for effective damping of the natural oscillations of the stand in the absence of any such drive means.

Tests have shown that in the case of a typical ceiling-suspended pillar-stand of the aforementioned kind, an initiated natural oscillatory movement having an amplitude of about 2 mm can be caused to cease practically completely within the space of about 5 seconds, with the use of two pendulums suspended in the lower part of the stand and having a length of about 0.8 m and an individual weight of about 10 kg.

Suitably, two such pendulums are used, one on each side of the pillar-stand, since the central space of the stand is required for other purposes, for example for housing means by which the pendulum arm can be displaced, rotated, turned and/or braked in relation to the stand.

The oscillatory movements of the pendulum or pendulums are suitably dampened by a rubber cushion or like means mounted in a suitable position in the stand. Normally, it is preferred to dampen only one side of the pendulum by means of such damping means, since the characteristic feature of a pendulum is that it will swing equal distances in both directions relative to an 0-line, and consequently an additional damping means on the other side of the pendulum would fulfil no function.

The use of a pendulum arrangement of the aforementioned kind also affords a number of additional advantages which cannot be achieved with hitherto known natural-oscillation damping arrangements. One such advantage resides in the fact that when a pillar-stand of the aforementioned kind is manufactured in the factory, the stand is fully assembled and tested in the aforesaid respect. When using a pendulum arrangement of the aforedescribed kind, the relative positions of the pendulum and the stand under ideal circumstances can be marked on suitable parts of the pendulum and stand. The pillar-stand is then dismantled, for transportation to the place where it is to be used, and re-assembled. The aforementioned marks can then be used to ensure that the pillar-stand is correctly assembled at its place of use.

The aforesaid principle can be applied to varying degrees of fineness. A measurement can be made on one or two sides by means of an infrasonic or ultrasonic transmitter of the deviation from the ideal value, and to take advantage hereof when adjusting the position of the pillar-stand. When the deviation from the ideal position on both sides is 0, it will be ensured that the pillar-stand is correctly adjusted.

One or more pendulums of the aforementioned kind can be replaced with, for example, a weight carried by ball bearings and having magnetic properties, and arranged for movement backwards and forwards in a magnetic field generated by permanent magnets or electro magnets. This enables the desired soft damping of the weight or body to be achieved in a simple fashion. The damping means may have a form other than the aforedescribed weight or body, however.

When the mass comprises a liquid contained in a container, the container is conveniently provided with a baffle which suitably extends in a direction so that movements of the liquid are effectively dampened in a direction which falls in the plane in which the pillar-stand exhibits the lowest inertia against natural oscillatory movement.

In a further improvement of the method according to the invention, means for sensing and/or registering the amplitude of the natural oscillatory movement or damping movement may be connected to X-ray exposure means carried by the stand, such as to prevent exposure at least for certain shutter times when the amplitude of the oscillations exceeds a given value.

This comparatively simple method ensures that no exposure can be made when the natural oscillatory movement would result in an unacceptable blurred X-ray picture.

The invention also relates to a movably mounted pillar-stand for carrying X-ray equipment, the main characterizing features of the stand being set forth in the claims.

Additional aspects of the invention are disclosed in the following description, which is made with reference to a number of selected embodiments, illustrated in the accompanying drawings.

BRIEF DESCRIPTION OF THE DRAWINGS

FIG. 1 is a perspective view of a ceiling-suspended pillar-stand for carrying X-ray equipment, in accordance with the present invention.

FIG. 2 is a perspective view in larger scale, illustrating the partially cut-away lower part of the stand illustrated in FIG. 1.

FIG. 3 is a cross-sectional view taken on the line III—III in FIG. 1.

FIG. 4 is a perspective view of the lower part of a stand according to FIG. 1 provided with a modified oscillation-damping arrangement.

FIG. 5 is a perspective view of another modified damping arrangement.

FIG. 6 is a perspective view of a ceiling-suspended pillar-stand in which the X-ray apparatus comprises a displaceable and pivotably adjustable hospital bed.

DESCRIPTION OF THE PREFERRED EMBODIMENTS

In FIGS. 1–3, the reference 1 identifies a movable ceiling-mounted pillar-stand for a carrying X-ray equipment. The stand is of an invert L-shape, the stand part 2 of which is of invert L-shape having an upper horizontal part 2a and a vertical part 2b which terminates at a distance from a support surface or floor 7.

The stand 1 has a U-shaped pendant-like part 3 which is displaceable along the vertical leg 2b of the pillar-stand and arranged for rotation around a horizontal axis (not shown) relative thereto. The displaceable and pivotable pendant-like part 3 carries X-ray equipment in the form of an X-ray emission device 4 and a cassetteholder 5 for an X-ray negative.

As beforementioned, the stand part 2 is suspended from a ceiling, namely from a swivel bearing 8 firmly mounted on the ceiling 9.

When the stand part 2 and/or the pendant-like part 3 are adjusted, natural oscillatory movements will be created in the plane exhibiting the lowest inertia against such oscillations, this plane lying along a central line or symmetry plane through the inverted L through the ceiling-suspension point.

If the damping means according to the present invention, hereinafter described, is rendered inoperative, for example by means of anchoring the pendulums 10 to the stand part by means of screw clamps (not shown), the amplitude of the natural oscillations of the frame at its lower part will approach 2 mm. A reduction to an amplitude of about 1 mm takes more than 30 seconds, and it is not until 60 seconds have passed that the natural oscillatory movement can be said to have ceased.

In order to stop the natural oscillatory movement more rapidly, there are used pendulums 10 having a length of about 0.8 m. The pendulums are pivotally mounted on a horizontal pivot 11. The pendulums may be made of steel and each has a weight of about 10 kg.

The pendulums 10 are arranged on mutually opposite side surfaces of the stand part 2, between reinforcing flanges extending vertically in said stand. The pendulums 10 are arranged to swing in the direction of the natural oscillations of the standpart 2. The pendulating movement of the pendulums is restricted by a rubber cushion 12 on one of the flanges 2c.

When the pillar-stand begins to oscillate at its natural frequency as a result of making the aforementioned adjustments, a counter-directional damped oscillatory movement is automatically generated by the pendulums 10, which causes the natural oscillatory movement to cease practically completely within the space of some 4 to 5 seconds.

FIG. 4 illustrates a modified damping arrangement in the form of a weight or body 10' having magnetic properties and being movable on ball or roller bearings 11'. Two permanent magnets or electromagnets 12' restrict movement of the body 10' when said body is set into motion by the natural oscillatory movement of the pillar-stand 2. When using an electromagnet, damping can be regulated by varying the voltage.

In this arrangement it is possible, by way of an alternative, to set the body 10' into motion by means of electromagnets 12', said movement being given a frequency different to the frequency of the natural oscillatory movement of the pillar-stand.

In the modification illustrated in FIG. 5, a body of liquid 10", for example oil, is contained in a container 15 located in the lower part of the stand. When the stand oscillates at its natural frequency, the liquid executes a splashing movement which dampens the natural oscillations of the stand. In order to improve the effect, the container 15 may be suitably provided with a baffle plate (not shown). The damping effect can also be modified by varying the amount of liquid in the container.

FIG. 6 illustrates a similar, ceiling-hung pillar-stand 2. The X-ray equipment of this embodiment comprises a hospital bed 5' which is displaceably and articulately mounted on the stand part 2. The natural oscillations created in the stand when adjusting the position of the hospital bed and negatively affecting the X-rays pictures taken with the aid of X-ray equipment (not shown) arranged separately of the pillar-stand 2 is reduced by means of the pendulums 10 pivotally arranged in the lower part of the stand. Thus, this arrangement will also extinguish the natural oscillatory movement of the stand within the space of a few seconds.

It should be mentioned that the aforementioned extinguishing time of from 4 to 5 seconds is normally long enough for the person operating the equipment to move from the stand to a position — behind a lead screen — from which the exposure can be made. Thus, the operator is able to make the exposure practically immediately from said isolated position.

FIG. 2 illustrates in chain lines an auxiliary means 16 for damping the oscillatory movement magnetically, for example.

In FIG. 3 there is illustrated at the bottom of the stand, in connection with respective pendulums 10, means 2d which, together with said pendulum, can be provided with markings which indicate the position adopted by a respective pendulum when the stand is ideally suspended. The markings can be made when testing the stand in the factory, prior to delivery. These markings enable the stand to be precisely positioned when mounting the same in the location where it is to be used.

The amplitude of the natural oscillatory movement or of the damping means can be sensed by means of a suitable device which is connected, via a data processor, to the exposure-release means of the X-ray equipment. In this way, it can be readily ensured that an exposure is only taken when the amplitude has been reduced to an acceptable value of any desired magnitude.

In a modified embodiment hereof, the maximum permitted amplitude may vary from case to case in correspondence with relevant exposure times. This is particularly favourable in respect of the pre-programming of exposure parameters, which is now a normal procedure.

One of normal skill in this art will realize that the damping arrangement itself may have a form different to those illustrated and above described.

Although the invention is primarily suited for ceiling-suspended pillar-stands, it will be understood that the invention can also be applied to other types of X-ray stands, such as floor-mounted stands or wall-mounted stands.

Should the pillar-stand exhibit substantially the same degree of inertia against natural oscillations in a number of directions, the damping means may comprise a pendulum which is journalled for rotation at one end thereof. the counter-directional pendulating movement of the pendulum will thus be dependent upon the direction in which the pillar-stand is caused to oscillate.

In the case of a floor-mounted stand, damping is improved when the pendulating mass, for example, the pendulum, is arranged in the upper part of the stand and is inversely directed, i.e. the attachment point is located lowermost.

We claim:

1. A movably mounted pillar-stand for carrying X-ray equipment, such as X-ray exposure equipment, a hospital bed, and the like, said pillar-stand comprising:

(a) mounting means for mounting a pillar-stand on a mounting surface for movement relative to the mounting surface;

(b) a supporting stand connected to the mounting means and extending outwardly from the mounting surface for supporting X-ray apparatus adapted for use with equipment for taking X-ray exposures, the supporting stand having a center of mass spaced from the mounting means; and (c) a mass carried by the pillar-stand at a mass mounting position on the supporting stand, the mass mounting position spaced from the mounting means and from the supporting stand center of mass, the mass having mounting means for mounting the mass on the supporting stand at the mass mounting position for pivotal movement relative to the mass mounting position and having a center of mass spaced from the mass mounting positon, the mass being movable relative to the supporting stand upon natural oscillatory movement of the supporting stand to execute a counter-directional damped pendulating movement in a manner to rapidly extinguish said natural oscillatory movement.

2. A pillar-stand according to claim 1, wherein the mass is positioned to pendulate in a plane which exhibits the lowest inertia to the natural oscillatory motion of the stand, and damping means carried by the supporting stand to restrict the amplitude of pendulation of the mass in said plane.

3. A pillar-stand according to claim 1, wherein the mass comprises a pendulum and the mass mounting means is journalled to the supporting stand at one end of the mass for oscillation of the mass about the mass mounting position.

4. A pillar-stand according to claim 1, wherein said stand is suspended from a ceiling; and the mass is positioned in a lower part of the stand.

5. A pillar-stand according to claim 1, wherein said mass is pivotally mounted on said supporting stand at a point between the supporting stand center of mass and an outer end of the supporting stand.

* * * * *